United States Patent [19]

Lyons

[11] Patent Number: 5,566,671
[45] Date of Patent: Oct. 22, 1996

[54] MEDICAL ACOUSTIC SENSOR RECEPTACLE

[76] Inventor: Chad Lyons, 51 Montoya Dr., Branford, Conn. 06405

[21] Appl. No.: 247,322

[22] Filed: May 23, 1994

[51] Int. Cl.$^6$ .................................................. A61B 5/04
[52] U.S. Cl. ................................. 128/639; 128/640
[58] Field of Search .................... 128/639, 640, 128/641; 206/461, 463, 965

[56] References Cited

U.S. PATENT DOCUMENTS

| | | |
|---|---|---|
| 1,637,829 | 8/1927 | Lurie . |
| 3,580,240 | 5/1971 | Cosentino . |
| 3,602,216 | 8/1971 | Moe . |
| 3,746,004 | 7/1973 | Jankelson . |
| 4,040,412 | 8/1977 | Sato . |
| 4,114,352 | 9/1978 | Horton et al. . |
| 4,213,463 | 7/1980 | Osenkarski . |
| 4,317,278 | 5/1982 | Carmon et al. . |
| 4,354,509 | 10/1982 | Strahwald et al. . |
| 4,524,087 | 6/1985 | Engel .......................... 128/639 |
| 4,583,548 | 4/1986 | Schmid ........................ 128/639 |
| 4,643,193 | 2/1987 | DeMarzo . |
| 4,768,514 | 9/1988 | DeMarzo ...................... 128/640 |
| 4,777,954 | 10/1988 | Keusch et al. ............... 128/640 |
| 5,197,472 | 3/1993 | Disabito ..................... 128/639 X |
| 5,269,810 | 12/1993 | Hull et al. .................. 128/639 X |
| 5,330,527 | 7/1994 | Montecalo et al. .......... 128/639 X |

FOREIGN PATENT DOCUMENTS

| | | | |
|---|---|---|---|
| 12402 | 6/1980 | European Pat. Off. | ............. 128/639 |
| 498527 | 2/1939 | United Kingdom . | |

*Primary Examiner*—Sam Rimell
*Attorney, Agent, or Firm*—DeLio & Peterson

[57] ABSTRACT

A receptacle for a piezoelectric medical acoustic sensor comprises a lower skin side layer of a sound transmitting conformable material, preferably provided with an adhesive for attachment to the skin of a patient, and an outer sound deadening layer of an elastic foam material which prevents the transmission of room noise to the sensor. The outer layer is adhered to the skin side layer to form a pocket and the elastic properties of the outer layer hold the sensor in close acoustic contact with the skin side layer to improve the signal to noise ratio for the sensor.

15 Claims, 1 Drawing Sheet

MEDICAL ACOUSTIC SENSOR RECEPTACLE

BACKGROUND OF THE INVENTION

1. Field of the Invention

This invention relates to holders used with medical sensors for electrically monitoring sounds such as the heartbeat or respiratory noises within a patient's body. More particularly, the invention relates to a receptacle used to hold a piezoelectric acoustic sensor in contact with a patient's body to provide an improved signal to noise ratio as compared to the conventional method of applying the sensor directly to the patient's skin.

2. Description of Related Art

The stethoscope has long been an important tool used by physicians to hear sounds within a patient's body for diagnosing disease and monitoring the health of the patient. However, interpreting the sounds is a relatively subjective task so that the comments one physician places in the patient's file may not be the same as those of another. Moreover, even though it is possible to record the sounds and to keep those recordings in the patient's file, tapes and other conventional sound recording media are bulky and awkward to store.

As a result, a new technology has been introduced into the market in which sounds and vibrations transmitted through a patient's body, such as the sounds produced by the heart or lungs, are detected by a sensor and, after appropriate amplification and filtering, are displayed visually. One method of display is to show the frequency spectrum of the sound as a function of time. Regardless of the form of the display, however, this procedure permits a visual display of the sounds which can be photographed, printed or stored electronically in the patient's file for further study. In general, this allows the sounds to be processed and handled in much the same way as an electrocardiogram is presently handled.

Such systems often provide spectral analysis of the sound signal and/or may provide highlighted marking of certain frequencies of interest of the physician to identify unusual noises or noises most likely to correspond to diseases. The most modern systems provide real time three dimensional display of the spectrum of heart and/or lung sounds on a high resolution color graphics monitor with specified frequencies and/or patterns being highlighted in a readily discernible color.

Systems of this type require a good sensor capable of producing a high quality electrical signal corresponding to the sounds transmitted through the patient's body. The sensor used is typically a piezoelectric sheet material having a surface area of a few tens of square centimeters. Sounds and vibrations passing through the patient cause the piezoelectric sensor to flex, generating a voltage which can be amplified, filtered and processed as desired.

Particularly where the sounds are to be analyzed spectrally, it is important for the sensor to provide a high signal level at all frequencies and to reduce noise to the minimum. It has heretofore been believed that the best method for obtaining the desired high signal to noise ratio is to apply the sensor directly to the skin of the patient at one or more desired acoustic sensing locations. This minimizes the number of interfaces that the sound must cross. At each interface there is the possibility that the sound will be attenuated. Commonly the acoustic sensor has been adhered directly to the skin of the patient with a temporary medical adhesive of the type used to attach electrocardiogram and other medical sensors.

This method has been found to have several problems, however. The step of applying the adhesive to the sensor is messy and time consuming. Moreover, once the adhesive is applied to the sensor it can be removed only with great difficulty and consequent risk of damage to the sensor. As a result, the sensor is usually discarded after a single use. A typical examination may use up to four or more sensors with a resulting high cost for each examination.

More importantly, the magnitude of the signal from sensors attached directly to the skin is limited and obtaining sufficient output is occasionally difficult. Yet another difficulty is that there are several types of noise that may be picked up by the sensor and mask the desired signal from the patient. Room noise is a common problem, particularly in emergency room settings or in pediatric care situations where the ambient noise levels are high. Because of the sensitivity of the sensor, objectionable noise is also produced whenever anything moves relative to the sensor or the patient in the vicinity of the sensor. "Cable noise" is the result of motion between the electrical cable connected to the piezoelectric sensor and the sensor. "Hair noise" occurs when the patient's body hair brushes the sensor as the patient breathes or moves. Other sources of objectionable noise exist, and all of these noise sources degrade the signal to noise ratio. In some settings the degradation can be so severe as to make it impossible to perform the desired analysis.

Another difficulty is that if a sensor is determined to be defective or if a different type of sensor must be used or tested, each sensor must be positioned at the same desired monitoring location on the patient's skin. Detaching an adhesively applied sensor from the skin once is uncomfortable. Detaching an adhesively applied replacement sensor from the same location where the previous sensor was positioned may be prohibitively uncomfortable to the patient.

Bearing in mind the problems and deficiencies of the prior art, it is therefore an object of the present invention to provide a receptacle for holding an acoustic sensor whereby the signal output by the sensor is increased.

A further object of the invention is to provide an acoustic sensor receptacle which decreases the detection of room noise, particularly in pediatric settings or in an emergency room and also decreases cable noise and noise associated with motion between the sensor and the patient's body such as noise produced by contact between the cable and the body or between hairs on the patient's body and the sensor.

It is another object of the present invention to provide an acoustic sensor receptacle which permits the sensor to be reused repeatedly without cleaning and without damage to the sensor.

A further object of the present invention is to provide an acoustic sensor receptacle which is relatively inexpensive and may be discarded after each use.

Still another object of the invention is to provide a medical acoustic sensor receptacle which produces an improved signal to noise ratio on heavier patients.

Yet another object of the present invention is to provide a medical acoustic sensor receptacle that permits a defective sensor to be easily and painlessly replaced without changing the sensing location of the sensor.

SUMMARY OF THE INVENTION

The above and other objects, which will be apparent to those skilled in the art, are achieved in the present invention which is directed to a receptacle for an acoustic sensor having an upper layer attached partially around the perimeter to a lower or skin side layer to form a pocket for receiving the sensor. The skin side layer is constructed of a material that transmits sounds and is sufficiently flexible to conform to the contours of the patient's body. The outer layer is constructed of a material that prevents or minimizes the transmission of sound and stretches.

The skin side layer of the receptacle is attached with adhesive to the patient's skin at the desired acoustic sensing location. When the sensor is inserted into the pocket between the two layers, the outer layer is stretched and holds the edges of the sensor in very tight acoustic contact with the skin side layer around the perimeter. The center of the sensor is held somewhat more loosely, but still in good acoustic contact with the skin side layer. The result of holding the sensor in this way is to produce an increased output signal as compared to the sensor attached directly to the skin.

The sensor is never contaminated with adhesive because it slips into the pocket formed by the two layers of the receptacle. As a result, it need not be cleaned after each use and lasts through many repeat uses. Moreover, the sensor may be replaced easily in the same location if the sensor is determined to be defective or a different sensor must be used. In the most highly preferred embodiment, the skin side layer has the adhesive preapplied and covered with a protective release film which is peeled off just before the sensor is attached to the patient's body.

The skin side layer is constructed of a thin, deformable, sound-transmitting material which allows it to conform to the shape of the patient's chest wall. A thin waterproof sheet of a synthetic material cut to a size just larger than the sensor has been found to work well. The upper layer is preferably constructed of a relatively thick, stretchable sound absorbing material. A stretchable medical foam in sheet form works well in this application to absorb sounds and reduce room noise while holding the sensor in the desired acoustic contact with the skin side layer.

The invention also includes the method of monitoring sounds within a patient's body comprising the steps of adhering an acoustic sensor receptacle constructed according to the description herein to the patient's body and inserting a substantially planar piezoelectric sensor into the pocket formed between the skin side and outside layers of the receptacle followed by monitoring sounds within the patient's body by analyzing the electrical signals produced by the sensor.

BRIEF DESCRIPTION OF THE DRAWINGS

For a fuller understanding of the invention, reference should be made to the following description taken in connection with the accompanying drawings, in which.

DESCRIPTION OF THE PREFERRED EMBODIMENT(S)

In describing the preferred embodiment of the present invention, reference will be made herein to FIGS. 1–3 of the drawings in which like numerals refer to like features of the invention. Features of the invention, particularly the thickness of the layers, are not necessarily shown to scale.

Figure 1:
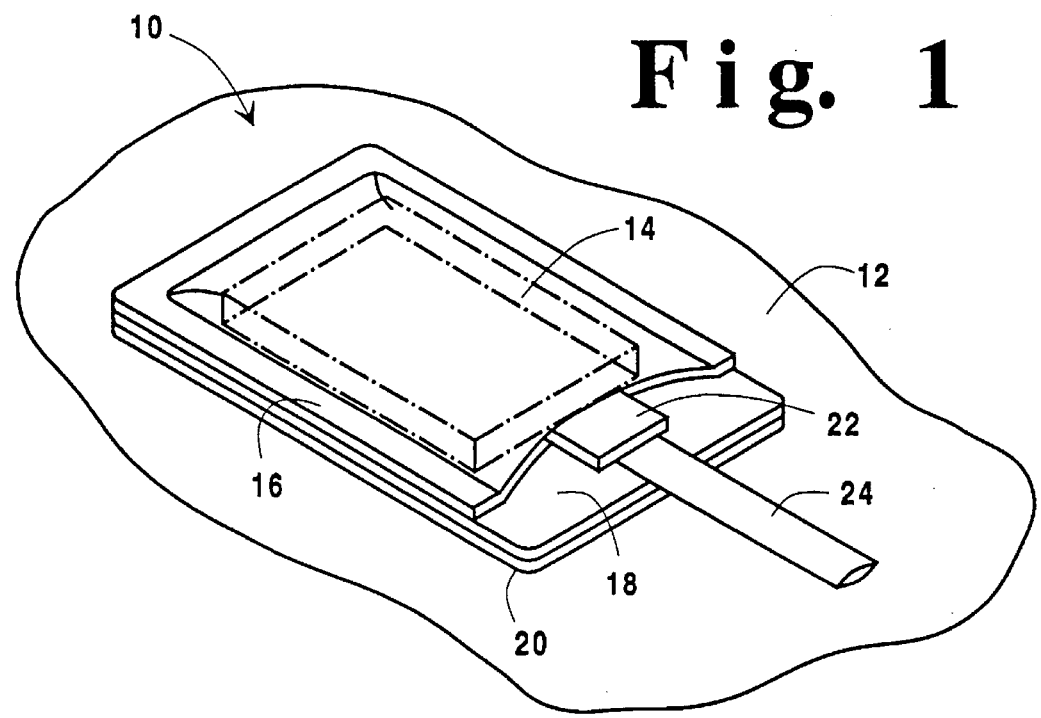
FIG. 1 is a perspective view of a medical acoustic sensor receptacle according to the present invention shown in perspective with a sensor inserted into the receptacle.
Figure 2:
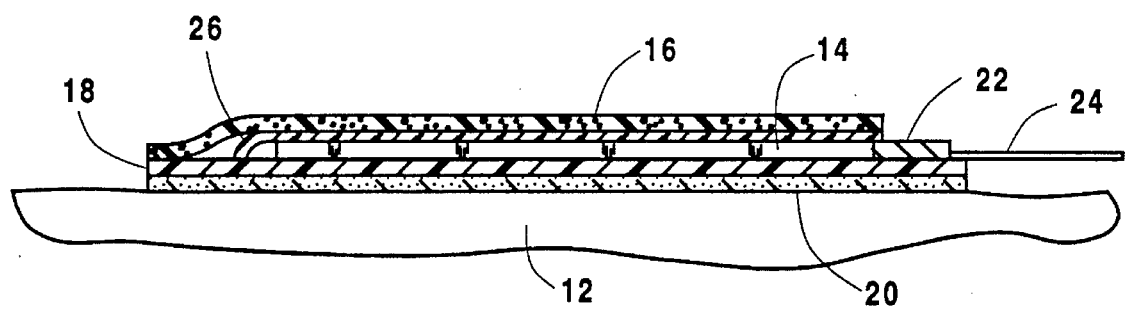
FIG. 2 is a cross sectional view from the side of the receptacle seen in FIG. 1.

FIGS. 1 and 2 show a first embodiment of the invention constructed of widely available medical sheet materials. The receptacle 10 is illustrated on the skin 12 of the patient holding a piezoelectric sensor 14 in a pocket formed between an outer layer 16 and a skin side layer 18. The skin side layer is applied to the skin of the patient with an adhesive layer 20. The adhesive may be applied as a paste or gel at the time the sensor adhered to the patient, or more preferably, the adhesive may be a conventional medical adhesive sold in sheet form between removable release films. Such adhesive films are used for attaching sensors, such as EKG sensors, to a patient. A suitable adhesive is a water based adhesive sheet material sold under the trade name "Hydrogel".

In the most highly preferred construction, the adhesive is applied to the skin side layer 18 when the receptacle is manufactured and covered with an easily removable release film (not shown) to protect the adhesive from contamination during shipment and handling. The release film is simply peeled off and discarded before application of the sensor to the patient. Such a release film may be used on the adhesive with either the embodiment shown in FIGS. 1 and 2 or with the embodiment shown in FIG. 3.

Referring to FIG. 1, the sensor 14 is connected through a plug 22 and a cable 24 to the monitoring equipment (which does not form part of the present invention). Such equipment will often include amplifiers, filters, spectrum analyzers and display equipment combined into a single cabinet.

The receptacle of the present invention is formed as a rectangle, with three sides around the perimeter of the upper layer bonded to the corresponding three sides of a rectangular lower layer to form the pocket into which the sensor is inserted. In the preferred design, the upper layer is slightly shorter in one dimension than the lower layer, but is long enough to fully enclose the sensor in the pocket. The longer skin side layer is believed to hold the cable away from the patient's skin in the immediate vicinity of the sensor to reduce cable noise. This also provides a barrier between the conductive components connected to the sensor and any adhesive or sound transmitting materials used between the receptacle and the patient's skin.

The lower skin side layer may be constructed of any material which transmits sound. It also must be conformable to the shape of the patient's chest wall or the desired acoustic sensing location and is most preferably a thin sheet of a waterproof plastic material such as a polyethylene film. A suitable material is a polyethylene flesh colored medical tape sold by Minnesota Mining and Manufacturing Company (3M) having Product No. 1523. This material has an adhesive pre-applied and is approximately 0.005 inches thick (0.127 millimeters). It is quite similar in appearance to the two adhesive ends of simple household bandages sold for covering small cuts and scrapes under the trademark "BAND-AID".

Material having any thickness may used for the lower layer provided that it is conformable to the patient's body (e.g. chest wall) where the monitoring will occur and transmits sound in an acceptable manner through the thickness used. A material having a thickness of less than 0.75 millimeters and preferably less than 0.25 millimeters is believed to be most suitable for the invention.

The outer layer 18 is a stretchable foam tape having both elastic and sound deadening properties. The sound deadening property reduces room noise and appears to provide an improved resistance to the coupling of sounds between the room and the patient's body. The elasticity of the outer layer holds the sensor 14 in close acoustic contact with the patient through the skin side layer.

The foam should provide the sound deadening property for reducing room noise while simultaneously providing elasticity to hold the sensor down against the skin side layer and the patient. The thickness should not be so great that the elasticity is hindered, nor so thin that room noise is not deadened. A suitable material is a polyvinyl chloride foam tape sold by 3M under Product No. 9777L. This material has a thickness of 0.034 inches (0.96 millimeters). The range of thicknesses that are effective will depend upon the intrinsic characteristics of the foam. Nonetheless, it is believed that foam materials having a thickness of at least 0.25 millimeters and, most preferably, at least 0.75 millimeters will be the most suitable.

Compared to the prior art method of directly applying the sensor to the skin, the sound must travel through an additional interface and an additional layer of material when the present invention is used. It might be believed that this would cause a reduction in the signal received by the sensor. Surprisingly however, tests have shown that not only is the noise reduced, but also the magnitude of the detected signal is increased.

Because the specific mechanism by which the signal is increased is unclear, the applicant does not wish to be bound by any theory of operation. However, it appears that the effect of the receptacle is to allow the sensor to flex more than it would if the sensor were to be adhesively applied directly to the patient's skin. The pocket seems to provide a wider and/or longer zone in which the piezoelectric sensor can flex, possibly by tightly pinning down the sensor at the edges where the upper and skin side layers are connected and more loosely in the center which yields a greater deflection in the middle of the sensor.

Regardless of the method of operation, the sensitivity of the sensor does not appear to depend critically upon the tension of the elastic material on the outer layer of the receptacle. Tests have shown that in addition to providing an increased signal, the receptacle decreases room noise, cable noise and hair noise. The receptacle is particularly valuable for use in noisy environments such as emergency room settings or in pediatric care situations where the resistance to room noise is important.

One problem that the prior art direct adhesive method has is that heavier patients appear to be more strongly coupled to room noise. Such patients may be very difficult to monitor due to the high noise level. The sensor receptacle of this invention provides a significantly improved signal relative to this noise and permits detection with acceptable signal to noise ratios even for heavier patients in relatively noisy environments.

Although the use of a sound deadening foam is most highly preferred, the invention is also operable to produce the increased signal with any outer layer having a desired elastic properties, however there may be little or no reduction in the noise.

FIG. 2 provides a cross sectional side view of the most highly preferred embodiment of the invention which uses the 3M brand foam tape and medical vinyl tape described above. The foam tape is provided with an adhesive over its entire underside. This adhesive is used to adhesively attach the upper layer to the skin side layer around the perimeter to define the pocket.

However, because the adhesive extends over the entire surface of the foam, it would adhere to the sensor or seal the pocket shut if permitted to do so. To prevent this, a thin sheet of latex 26 is applied to the underside of the outer foam layer within the region of the foam layer corresponding to the pocket. This prevents the adhesive on the foam from contacting the sensor or the skin side layer except at the perimeter on three sides of the pocket.

The latex sheet has elastic properties which cooperate with the elastic properties of the foam sheet. The latex also provides a non slip surface which holds the sensor in the desired position. The preferred latex material is a film about 0.008 inches thick (0.2 millimeters).

Figure 3:
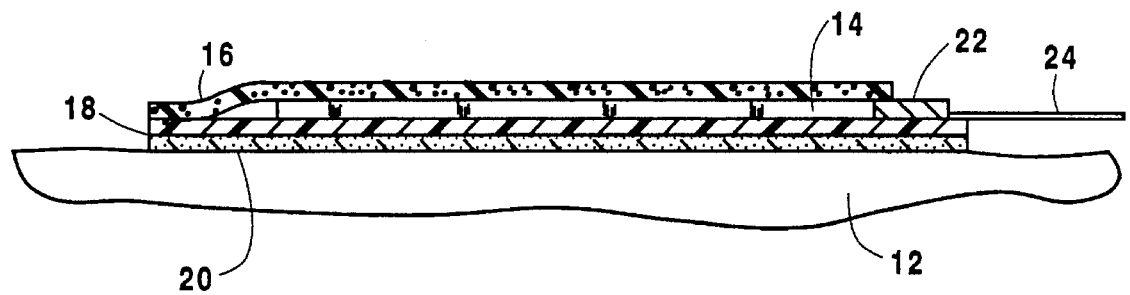
FIG. 3 is a cross sectional view from the side of an alternative embodiment of the receptacle of the present invention.

FIG. 3 shows an alternative embodiment of the invention in which the upper layer is constructed of an elastic foam material which does not have adhesive over its entire surface. Thus the latex layer 26 is not required. The outer layer of foam is bonded easily with an adhesive, heat or any other suitable means around three sides to form the desired pocket.

Although the invention contemplates various configurations for the outer layer and skin side layer, the configuration shown in FIG. 1 is preferred in which the outer layer has a slightly shorter length longitudinally then the inner layer. It is believed that this helps to provide the minimum cable noise. Other configurations, however, may also be satisfactory, such as a circular configuration or a configuration in which the outer layer and the skin side layer are of the same shape.

The noise produced by motion between the patient's body and the sensor such as by contact between hair and the sensor is also minimized by the use of the receptacle of the invention. The adhesive layer on the skin side which is slightly larger than the sensor traps hairs and prevents them from moving while the sensor is active.

Thus, having described the invention,
What is claimed is:

1. A medical acoustic sensor receptacle comprising:
   an outside layer and a skin side layer attached together to form a pocket, the pocket having an opening allowing a medical acoustic sensor to be inserted into and removed from the pocket, the medical acoustic sensor being responsive to acoustic signals transmitted through the body of a patient;
   the skin side layer being constructed of a sound transmitting sheet material having sufficient flexibility to permit the skin side layer to deform into close acoustic contact with the skin of the patient at each desired acoustic sensing location on the patient; and
   the outside layer being constructed of a stretchable elastic material that stretches to receive the medical acoustic sensor when the medical acoustic sensor is inserted into the pocket, the elastic properties of the stretchable material providing an elastic holding force to hold the medical acoustic sensor into close acoustic contact with the skin side layer when the medical acoustic sensor is inserted into the pocket.

2. A medical acoustic sensor receptacle according to claim 1 further including a medical adhesive layer bonded to the skin side layer for temporarily adhesively attaching the receptacle to the patient's skin.

3. A medical acoustic sensor receptacle according to claim 2 further including a release film layer releasably adhered to the medical adhesive layer for protecting the medical adhesive layer during shipment and handling.

4. A medical acoustic sensor receptacle according to claim 1 wherein the stretchable elastic material of the outside layer is a stretchable foam having sound absorbing properties.

5. A medical acoustic sensor receptacle according to claim 4 wherein the stretchable foam layer is at least 0.25 mm thick.

6. A medical acoustic sensor receptacle according to claim 5 wherein the stretchable foam layer is at least 0.75 mm thick.

7. A medical acoustic sensor receptacle according to claim 1 wherein the stretchable elastic material of the outside layer comprises:

a stretchable foam layer, having sound absorbing properties, extending across substantially the entire width of the receptacle, an adhesive layer extending across substantially the entire width of the receptacle and adhering a portion of the perimeter of the stretchable foam layer to the skin side layer along a corresponding portion of the perimeter of the skin side layer, another portion of the perimeter of the stretchable foam layer and the skin side layer defining the opening for receiving the medical sensor, and a stretchable film layer extending across a portion of the surface of the adhesive layer to prevent the adhesive layer from contacting the sensor, the stretchable film layer having elastic properties cooperating with the elastic properties of the stretchable foam layer to hold the sensor into close acoustic contact with the skin side layer when the medical sensor is inserted into the pocket.

8. A medical acoustic sensor receptacle according to claim 7 wherein the stretchable film layer comprises a stretchable latex.

9. A medical acoustic sensor receptacle according to claim 1 wherein the skin side layer comprises a waterproof, man-made substantially inelastic material.

10. A medical acoustic sensor receptacle according to claim 1 wherein the skin side layer comprises vinyl.

11. A medical acoustic sensor receptacle according to claim 1 wherein the skin side layer is less than 0.25 mm thick.

12. A medical acoustic sensor receptacle comprising:

an outside layer and a skin side layer attached together to form a pocket having an opening for receiving a medical sensor responsive to acoustic signals transmitted through the body of a patient;

the skin side layer being constructed of a sound transmitting sheet material having sufficient flexibility to permit the skin side layer to deform into close acoustic contact with the skin of the patient at each desired acoustic sensing location on the patient;

the outside layer including:

a stretchable foam layer, having sound absorbing properties, extending across substantially the entire width of the receptacle, an adhesive layer extending across substantially the entire width of the receptacle and adhering a portion of the perimeter of the stretchable foam layer to the skin side layer along a corresponding portion of the perimeter of the skin side layer, another portion of the perimeter of the stretchable foam layer and the skin side layer defining the opening for receiving the medical sensor, and a stretchable film layer extending across a portion of the surface of the adhesive layer to prevent the adhesive layer from contacting the sensor, the stretchable film layer having elastic properties cooperating with the elastic properties of the stretchable foam layer to hold the sensor into close acoustic contact with the skin side layer when the medical sensor is inserted into the pocket;

a medical adhesive layer bonded to the skin side layer for temporarily adhesively attaching the receptacle to the patient's skin; and a release film layer releasably adhered to the medical adhesive layer for protecting the medical adhesive layer during shipment and handling.

13. A medical acoustic sensor receptacle adapted to receive a medical acoustic sensor comprising:

an elastic outside layer attached to a skin side layer to form a pocket for releasably holding the sensor;

the skin side layer being constructed of a sound transmitting sheet material having sufficient flexibility to permit the skin side layer to deform into close acoustic contact with the skin of the patient;

the elastic outside layer stretching when the sensor is inserted into the pocket to provide an elastic holding force to hold the sensor in acoustic contact with the skin side layer, the elastic holding force being greater at the perimeter of the pocket than at the center of the pocket; and a medical adhesive layer bonded to the skin side layer for temporarily adhesively attaching the receptacle to the patient's skin.

14. A medical acoustic sensor receptacle according to claim 13 further comprising a release film layer releasably adhered to the medical adhesive layer for protecting the medical adhesive layer during shipment and handling.

15. A method of monitoring sounds within a patient's body comprising the steps of:

adhering an acoustic sensor receptacle to the skin of the patient at a desired acoustic sensing location on the patient, the acoustic sensor receptacle comprising:

a substantially planar outside layer having a perimeter and a substantially planar skin side layer having a perimeter attached together along a portion of the respective perimeters of the layers to form a pocket for releasably holding a piezoelectric medical acoustic sensor having an inner side and an outer side, the skin side layer being constructed of a sound transmitting sheet material having sufficient flexibility to permit the skin side layer to deform into close acoustic contact with the skin of the patient at the desired acoustic sensing location, and the outside layer being constructed of a stretchable elastic material;

inserting the piezoelectric medical acoustic sensor into the receptacle between the outside layer and the skin side layer, the outer layer of the receptacle contacting the outer side of the sensor and elastically holding the inner side of the sensor in close acoustic contact with the skin side layer of the receptacle; and monitoring the sounds within the patient's body by monitoring electrical signals produced by the sensor.

* * * * *